United States Patent [19]

Birke et al.

[11] 3,991,058

[45] Nov. 9, 1976

[54] PROCESS FOR DRYING CHEMICAL PRODUCTS USING A BURNABLE ORGANIC LIQUID SUCH AS METHANOL

[75] Inventors: Walter Birke; Hans-Ulrich von der Eltz; Franz Schön, all of Frankfurt am Main, Germany

[73] Assignee: Hoechst Aktiengesellschaft, Frankfurt am Main, Germany

[22] Filed: Dec. 17, 1974

[21] Appl. No.: 533,656

Related U.S. Application Data

[63] Continuation of Ser. No. 302,852, Nov. 1, 1972, abandoned.

[30] Foreign Application Priority Data

| | | |
|---|---|---|
| Oct. 12, 1972 | Germany | 2230236 |
| Oct. 12, 1972 | Germany | 2250005 |
| Oct. 12, 1972 | Germany | 2249932 |

[52] U.S. Cl. .................................... 260/282; 8/80; 8/81; 34/1; 34/4; 34/9; 34/33; 34/42; 106/310; 203/88; 260/208; 260/701; 260/704

[51] Int. Cl.$^2$ ................ C07B 29/00; C07C 107/00; C07D 235/04; C09B 43/00

[58] Field of Search ........... 260/208, 282, 701, 704; 8/80, 81; 203/88; 34/1, 4, 9, 33, 42; 106/310

[56] References Cited

UNITED STATES PATENTS

| | | | |
|---|---|---|---|
| 2,138,049 | 11/1938 | Vesce | 260/704 UX |
| 2,282,303 | 5/1942 | Morrison et al. | 260/704 UX |
| 2,437,397 | 3/1948 | McLemore | 8/140 X |
| 2,819,258 | 1/1958 | Schmid et al. | 260/140 |
| 3,049,533 | 8/1962 | Spitzer et al. | 260/197 |
| 3,056,642 | 10/1962 | Kesler et al. | 260/208 X |
| 3,071,815 | 1/1963 | MacKinnon | 260/208 X |
| 3,305,937 | 2/1967 | Gutwirth et al. | 34/17 |
| 3,575,957 | 4/1971 | Demler et al. | 260/163 |
| 3,905,764 | 9/1975 | Birke et al. | 8/140 |
| 3,909,196 | 9/1975 | Birke et al. | 8/140 |

OTHER PUBLICATIONS

Miehr et al., Chemical Abstracts, vol. 24, p. 2688 (1930).

*Primary Examiner*—Floyd D. Higel
*Attorney, Agent, or Firm*—Curtis, Morris & Safford

[57] ABSTRACT

Process for drying chemicals which comprises treating the chemicals with a burnable organic liquid and burning off the liquid to dry the chemicals.

The process is particularly useful for drying chemicals such as dyestuffs, pharmaceuticals and organic intermediates by applying an aqueous methanol solution to the chemicals and burning off the methanol to dry the chemicals.

13 Claims, 1 Drawing Figure

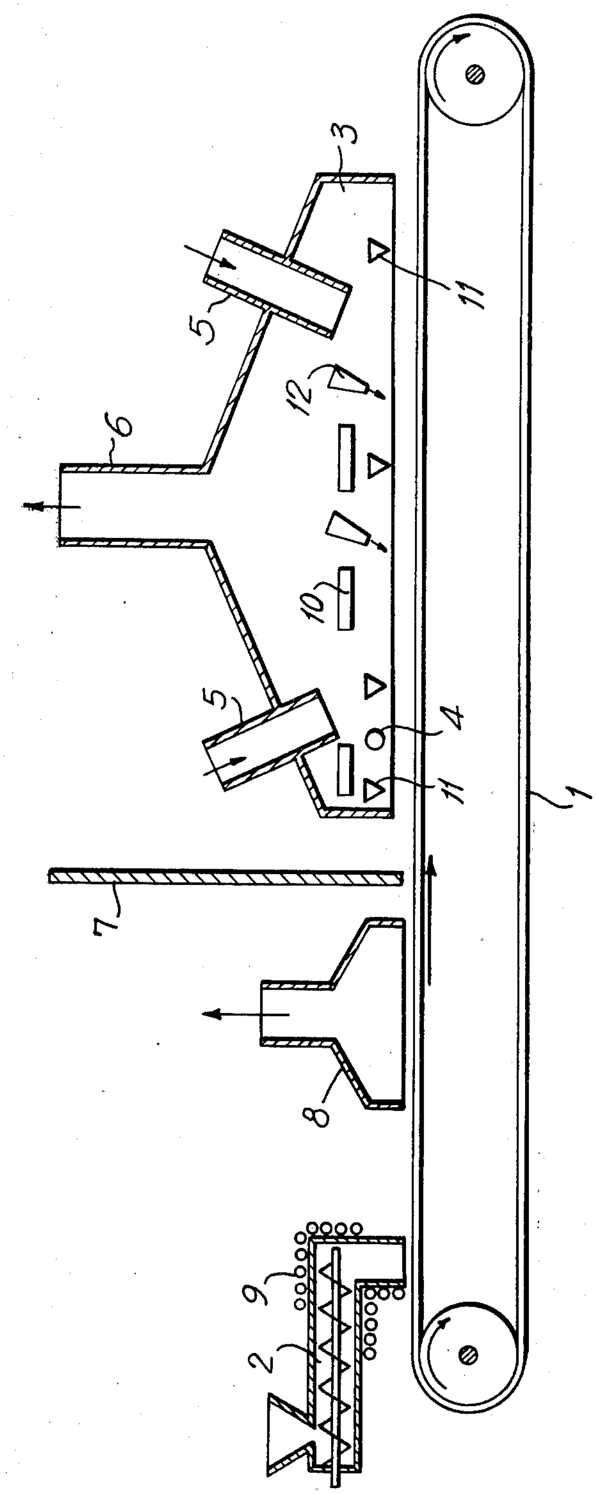
3
11
5
12
6
10
5
4
11
1
7
8
9
2

PROCESS FOR DRYING CHEMICAL PRODUCTS USING A BURNABLE ORGANIC LIQUID SUCH AS METHANOL

This is a continuation of application Ser. No. 302,852, filed Nov. 1, 1972, now abandoned.

The present invention relates to a process for drying chemical products, in which the products are treated with a burnable liquid preferably methanol and this is subsequently burnt off.

According to the process of the present invention it is possible to dry a number of chemical products in solid form, such as dyestuffs, pharmaceutical products or organic intermediates. Those substances are, by their nature, not suitable which, in combination with methanol, have undesired chemical reactions. Of special importance is the process for drying those substances which, when being prepared, are obtained in the form of methanolic solutions and suspensions or as presscakes moist by methanol. In order to be able to control better the burning off process, it is often recommendable to work, not with pure methanol but with methanol/water mixtures, containing up to 70 % by volume, preferably 20 to 50 % by volume of water. That is to say that the necessary amount of methanol which, in the case of products which occur in the form of aqueous solutions or suspensions, can also be added subsequently, or the products can be isolated by filtering off, suction-filtering or squeezing off and the residue is washed out with methanol. As well as methanol, also other burnable organic solvents can be used separately or in mixture with methanol.

The products moistened with methanol or a methanol/water mixture are introduced into a suitable burning off device, where the methanol vapors are ignited by an igniting device and the products are dried completely in this way. By varying the water content the remaining moisture content may be controlled after drying. If pure methanol is used, for example at room temperature, or with addition of small amounts of water, it is sufficient to ignite the vapors once only. In the case of high water contents, that is if the ignition point is above room temperature, it is necessary to insure a continuous ignition, for example by several gas flames.

In the case of longer and above all continuous drying processes it is recommendable for reasons of safety to adjust the products to be dried before burning to temperatures of below the ignition point of the burnable liquid used. In general, temperatures of from 1° to 40° C, preferably 1° to 15° C, below the corresponding ignition point are sufficient. This can be brought about by cooling the products to be dried and/or by using liquids, for example methanol/water mixtures, the ignition points of which are above room temperature.

In the process claimed it has also been found that more advantageous results can be obtained, if the burning off process is effected in connection with drying systems already known, i.e. with additional supply of heat.

If the products to be dried are heated above the ignition point, for example by an infrared heating device or gas irradiators, in general, one ignition is sufficient. The ignition is expediently carried out in direct proximity to the heating device. Additional heating devices along the burning off area are also advantageous, if moist products are used which contain a high proportion of water.

The type of the burning off device depends to a large extent on the type and quantity of the product to be dried. In the simplest case the material to be dried is placed in a flat metal, stone, clay or enamel trough and the methanol vapors are ignited. A device suitable for a continuous process and to which the present invention also refers, essentially consists of a conveyer belt 1, on which the material to be dried is passed through a worm 2 or another suitable dosage device. This dosage device can expediently be equipped with a cooling device 9, which consists, for example, of cooling spirals. Furthermore, it is advantageous if further cooling elements are available for cooling the conveyor belts. The material is transported on the conveyer belt into the burning off chamber 3, at the inlet opening of which the ignition device 4, for example an electric ignition element or a flame, is attached.

The openings 5, serve for supplying the burning air. The hot waste gases leave the burning off chamber by the outlet opening 6; they can be used for further heating purposes. In order to insure the safety of the equipment, a firm wall 7 and a ventilation device 8 are situated above the conveyer belt in front of the burning off chamber; through this ventilation device inflammable vapors are exhausted by suction from the room in front of the burning off chamber. By photo cells, thermo sensers or other controlling apparatuses the burning off process can be controlled; in this way controlling apparatuses, which are fixed either in front of or behind the ignition device, can regulate for example in the case of the running back flame the conveyer belt speed, influence the ignition device and different safety devices, as for example throttle or stop the supply of air 5 and, if desired, introduce instead of air, gases which are not burnable or do not maintain the burning off process.

Above the conveyer belt running in the drying chamber, there may be heating devices 10 which on one hand heat the burnable liquid above its ignition point and, on the other, promote the evaporation of the burnable liquid or of the water. Along the drying area controlling equipment 11 is attached for drying, regulating of the speed dependently of the burning area and for the safety equipment. For example air nozzles 12 also affixed on a swivel along the burning area, regulate the flame.

If solution or thin suspensions are to be dried, it is also possible to spray the solutions or suspensions in a tower, in which a flame ignites the methanol vapors.

The advantage of the process of the invention is that chemical products can be dried simply and, if desired, practically without expenditure of additional energy and that, especially when using methanol, no materials are produced by the burning off process which pollute air or water.

A concrete example for a device according to the invention is illustrated as side view in the drawing mentioned below.

EXAMPLE

The press cake washed with methanol, and which was obtained according to Example 1 of German Patent Specification No. 1 279 260 was spread out in an even thin layer on a tin and ignited at one place by a flame. After all the methanol had been burnt off and the flames extinguished, the dry dyestuff was obtained in a finely divided form.

We claim:

1. A process for drying chemicals in solid form which consists essentially of applying to said chemicals a burnable organic liquid, igniting the liquid, burning off the liquid from the chemicals and thus drying the chemicals.

2. The process of claim 1 wherein an aqueous methanol solution containing up to 70% by volume of water is used as the burnable liquid applied to said chemicals.

3. The process of claim 1 wherein the chemicals, prior to the burning off step, are cooled to temperatures below the ignition point of the burnable liquid and are maintained at these temperatures until the ignition of the burnable organic liquid.

4. The process of claim 3 wherein, prior to the burning off step, the chemicals are cooled to temperatures 1° to 15° below the ignition point of the burnable liquid.

5. A process for drying a dyestuff in solid form which consists essentially of applying to the dyestuff a burnable organic liquid, igniting the organic liquid on said dyestuff, burning the liquid from the dyestuff and drying the dyestuff.

6. A process for drying a dyestuff in solid form which consists essentially of applying to the dyestuff, as a burnable liquid, methanol or an aqueous methanol solution containing up to 70% by volume of water, igniting and burning the methanol from the dyestuff and thereby drying the dyestuff.

7. The process defined in claim 6 wherein the burnable liquid is methanol.

8. The process defined in claim 7 wherein the burnable liquid is an aqueous methanol solution containing up to 70% by volume of water.

9. The process defined in claim 6 wherein the burnable liquid is an aqueous methanol solution containing 20 to 50% by volume water.

10. A process for drying a dyestuff in solid form which consists essentially of applying to the dyestuff an aqueous methanol solution containing 20 to 50% by volume water, igniting the methanol on said dyestuff, burning the methanol from the dyestuff and drying the dyestuff.

11. The process of claim 1 wherein the chemicals are selected from the group consisting of pharmaceuticals.

12. The process of claim 1 wherein the chemicals are selected from the group consisting of organic chemical intermediates.

13. The process of claim 1 wherein the burning off step is undertaken with additional heat supplied from heating devices provided along the burning-off area.

* * * * *

UNITED STATES PATENT AND TRADEMARK OFFICE

CERTIFICATE OF CORRECTION

PATENT NO. : 3,991,058

DATED : November 9, 1976

INVENTOR(S) : Birke et al.

It is certified that error appears in the above-identified patent and that said Letters Patent are hereby corrected as shown below:

In the Heading, Item [30], line 2, replace

"October 12, 1972 Germany 2230236" by

--June 21, 1972 Germany 2230236--.

Signed and Sealed this

Twenty-eighth Day of December 1976

[SEAL]

*Attest:*

RUTH C. MASON
*Attesting Officer*

C. MARSHALL DANN
*Commissioner of Patents and Trademarks*